United States Patent [19]
Askanazi et al.

[11] Patent Number: 5,006,559
[45] Date of Patent: Apr. 9, 1991

[54] METHOD OF USE OF BRANCHED-CHAIN AMINO ACIDS INFUSIONS TO INFLUENCE APPETITE

[75] Inventors: Jeffrey Askanazi; Karen Gil, both of Haworth, N.J.

[73] Assignee: Clintec Nutrition Co., Deerfield, Ill.

[21] Appl. No.: 328,842

[22] Filed: Mar. 27, 1989

Related U.S. Application Data

[63] Continuation-in-part of Ser. No. 238,709, Aug. 31, 1988.

[51] Int. Cl.$^5$ .............................................. A61K 31/195
[52] U.S. Cl. .................................................... 514/561
[58] Field of Search .......................................... 514/561

[56] References Cited

U.S. PATENT DOCUMENTS 4,210,637  7/1980  Wurtman et al. .................... 424/180
4,542,123  9/1985  Wurtman ................................ 514/3

OTHER PUBLICATIONS

Burzetein et al., Post Adsorptive Control of Food Intake in Healthy Humans, 2 FASEB 6 (1988).
MacGregor et al. Rate of Gastric Emptying of Solid Food in Man by High Caloric Parenteral Nutrition. The American Journal of Surgery, vol. 138, Nov. 1979.
Berstein et al., *An Experimental Test on the Glucostatic Theory of Regulation to Food Intake*, 35 J. Clintec Inves. 627 (1965).
Blundell, *Is There a Role for Serotonin (5-hydroxytryptamine) in Feeding?*, 1 Int'l Journal of Obesity 15 (1977).
Campbell et al., *Studies of Food-Intake Regulation in Man*, 25 The New England J. of Med. 1402 (1971).
Duncan et al., *The Effects of High and Low Energy Density Diets on Satiety, Energy Intake, and Eating Time of Obese and Nonobese Subjects*, 37 The Amer. J. of Clin. Nut. 763 (1983).
Elwyn et al., *Changes in Nitrogen Balance of Depleted Patients with Increasing Infusions of Glucose*, 32 The Amer. J. of Clin. Nut. 1597 (1979).
Fenstrom, *Effects of Protein and Carbohydrate Ingestion of Brain Tryptophan Levels and Serotonin Synthesis: Putative Relationship to Appetite for Specific Nutrients*, Interaction of the Chemical Senses with Nut. pp. 395–414 (1986).
Friedman et al., *The Physiological Phychology of Hunger: A Physiological Prospective*, 83 Psycho. Rev. 409 (1976).
Gil et al., *Reduction in Food Intake With Intravenous Nutrition in Healthy Males*, 5 Clin. Nut. 103 (1986).
Grinkler et al., *The Effects of Intravenous Administration of Glucose, Saline and Mannitol on Meal Regulation in Normal-Weight Human Subjects*, 6 Comm. in Behavioral Bio. 203 (1971).
Jordan et al., *Hunger and Satiety in Humans During Parenteral Hyperalimentation*, 36 Psychosomatic Med. 144 (1974).
Mellinkoff, *Relationship Between Serum Amino Acid Concentration and Fluctuations in Appetite*, 8 J. of App. Phys. 535 (1956).
Proikos et al., *Caloric Regulation in Normal-Weight Men Maintained on a Palatable Diet of Conventional Foods*, 29 Physi. and Beh. 293 (1983).
*Post Absorptive Control of Food Intake in Healthy Humans*, FASEB Journal, vol. 2, 1988.

(List continued on next page.)

*Primary Examiner*—Stanley J. Friedman
*Assistant Examiner*—Zohreh A. Fay
*Attorney, Agent, or Firm*—Hill, Van Santen, Steadman & Simpson

[57] ABSTRACT

This invention is a method of influencing voluntary food intake of patients receiving parenteral infusions, by adding branched-chain amino acids to the infusion solution. The branched-chain amino acid solution prevents total parenteral suppression of appetite and increases oral voluntary food intake. The branched-chain amino acid solution lowers the risk of regurgitation and aspiration in patients for uhm preoperative nutritional support and is an essential part of therapy.

7 Claims, 3 Drawing Sheets

OTHER PUBLICATIONS

Skeie, *Effects of a Branched Chain Amino Acid Enriched PN Solution on Voluntary Food Intake*, 6 Clin. Nut. 15 (1987).

Smyth, *The Effect of Orally and Intravenously Administered Amino Acid Mixtures on Voluntary Food Consumption in Normal Men*, 26 The J. of Clin. Inv. 439 (1946).

Spencer et al., *A System for Continuous Measurement of Gas Exchange and Respiratory Functions*, 33 J. of App. Physio. 523 (1972).

Spiegel, *Caloric Regulation of Food Intake in Man*, 34 J. of Compara. and Physio. Psych. 24 (1973).

Sriram et al., *Suppression of Appetite by Parenteral Nutrition in Humans*, 3 J. of Amer. College of Nut. 317 (1984).

Takala et al., *Changes in Respiratory Control Induced by Amino Acid Infusions*, Crit. Care Med. 465 (1988).

Welch et al., *Effect of Ileal and Intravenous Infusions of Fat Emulsions on Feeding and Satiety in Human Volunteers*, 89 Gastroenterology, 1293 (1985).

Woods et al., *Suppression of Food Intake by Intravenous Nutrients and Insulin in the Baboon*, 247 American Journal of Physiology R393 (1984).

Wooley et al., *Long-Term Food Regulation in Obese and Nonobese*, 33 Psychosomatic Medicine 436 (1971).

METHOD OF USE OF BRANCHED-CHAIN AMINO ACIDS INFUSIONS TO INFLUENCE APPETITE

RELATED APPLICATIONS

This is a continuation-in-part of U.S. patent application Ser. No. 238,709, filed on Aug. 31, 1988.

BACKGROUND OF THE INVENTION

A reduction in food intake and rapid satiation in patients receiving standard parenteral nutrition has been observed Jordan et al., *Hunger and Satiety in Humans During Parenteral Hyperalimentation,* 36 Psychosomatic Med 144 (March, 1974). This difficulty in making the transition from intravenous to oral feeding frequently prolongs the need for nutritional support and can delay the return to normal lifestyle. Additionally, a slowed rate of gastric emptying of solid foods in patients has been observed in patients receiving high caloric parenteral nutrition. MacGregor et al, *Slowed Rate of Gastric Emptying of Solid Foods in Man by High Caloric Parenteral Nutrition,* 138 Am J. Surg. 652 (1979). A delay in gastric emptying represents an important and non-negligible risk of aspiration in the immediate preinoperative period.

SUMMARY OF THE INVENTION

The invention is a method to facilitate the transition from parenteral to oral feeding and enhance oral intake in patients receiving parenteral nutrition but have some G.I. function, by parenterally administering to a patient a branched-chain amino acid solution. The branched-chain amino acid solution prevents total parenteral nutrition suppression of appetite and increases oral voluntary food intake. In particular, branched-chain amino acid solutions can be used to increase oral intake in patients with partially functional gastrointestinal tracts such as in AIDS and cystic fibrosis.

This invention also is a method to increase voluntary food intake of patients during or after the infusion of parenteral amino acid solution comprising about:

| L-Amino-Acids | mM/DL |
|---|---|
| Leucine | 9.56 |
| Isoleucine | 9.08 |
| Valine | 9.51 |
| Phenylalanine | 0.76 |
| Methionine | 0.77 |
| Lysine | 1.41 |
| Histidine | 0.55 |
| Threonine | 1.25 |
| Tryptophan | 0.22 |
| Alanine | 4.10 |
| Glycine | 4.87 |
| Arginine | 1.61 |
| Proline | 2.31 |
| Tyrosine | 0.07 |
| Serine | 1.14 |

The invention is also a method to improve gastric emptying by increasing branch-chain amino acids either parenterally or enterally. In particular, a method to lower the risk of regurgitation and aspiration for whom preoperative nutritional support includes parenterally administered branched chain amino acid enriched solutions.

The invention is also a method to reduce the risk of aspiration pneumonia in elderly patients in nursing homes through the mechanism of improved gastric emptying, by increasing levels of branched-chain amino acids in either enteral or parenteral nutrition.

DETAILED DESCRIPTION OF THE INVENTION-PREFERRED EMBODIMENT

Figure 1:
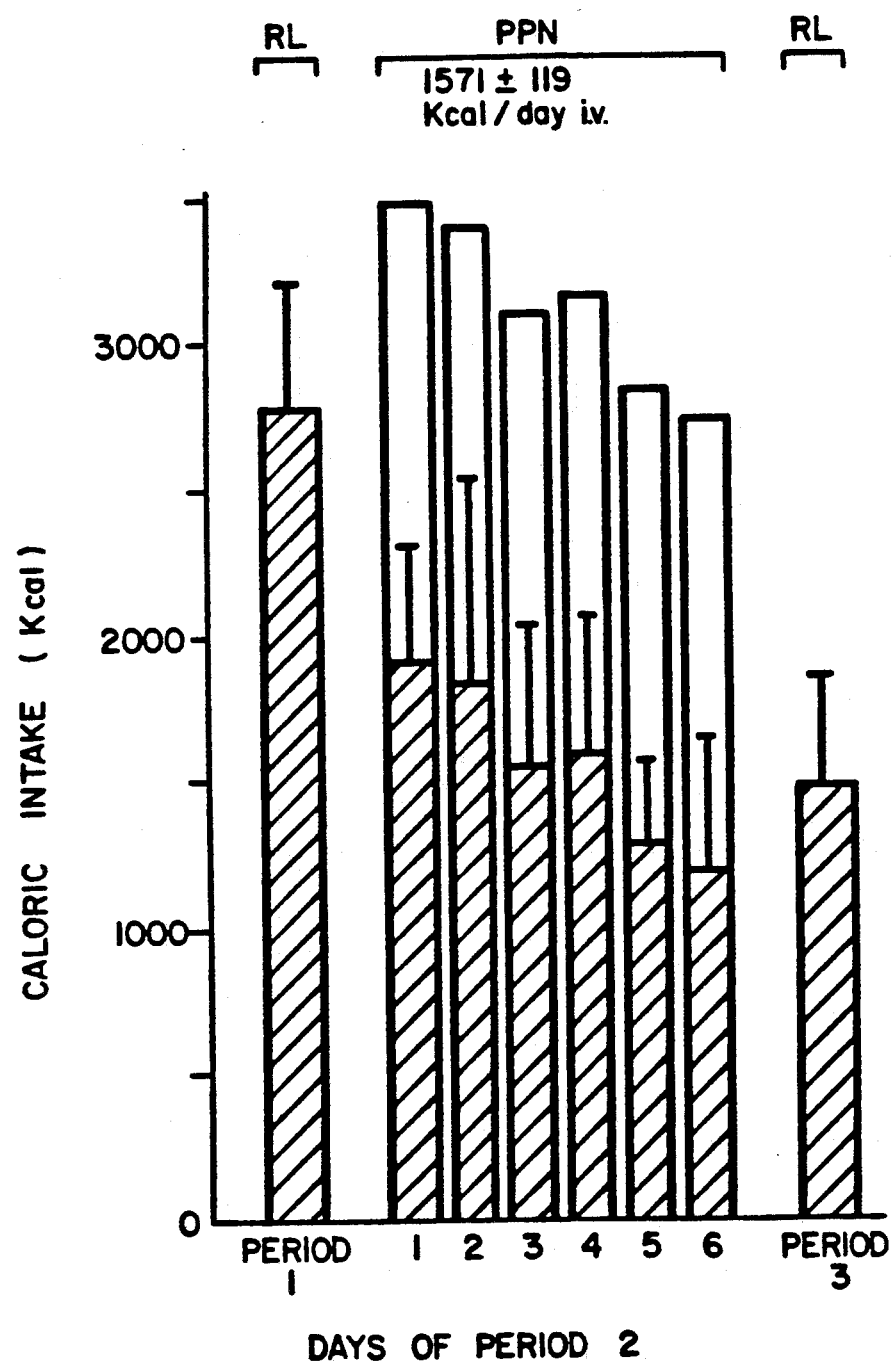
FIG. 1 shows oral (dark) and intravenous (speckled) caloric intake in four subjects receiving Ringer's Lactate (Period 1), PPN (Period 2), and Ringer's Lactate (Period 3). Mean±SEM.

Clinicians often view a return of normal appetite as a sign of recovery from illness. If TPN results in satiety, this may confound the clinical evaluation; one could surmise that TPN, if not carefully applied, could delay discharge from hospital care by obscuring the important clinical signs of recovery of appetite. The present discovery suggests that the use of branched-chain amino acid, by stimulating oral intake, may be useful for short term postoperative TPN; this would allow the beneficial effects of nutritional support while obviating any delay in return of appetite. The BCAA might also be useful in patients on home TPN.

EXAMPLE 1

Healthy male subjects (18 to 30 years of age) of normal weight who expressed no desire to lose or gain weight, were not concerned about their food intake, and had no history of diabetes, renal, hepatic or cardiovascular disease, participated in a formal lunchtime interview during which they were asked to consume the liquid diet used in this experiment (Ensure TM (Ross Laboratories, Columbus, Ohio)). They were told to eat as much as they wanted and, although they were unaware that intake of at least 300 ml had been selected as one of the admission for the 17–19 day study. The liquid diet was given in cans with the labels removed to prevent subjects from learning its composition and caloric content. Ensure TM was chosen for two reasons. First, it allowed for ease of measurement of caloric intake. Second, it was palatable but did not encourage overeating. Although perfect compliance during the week at home was desirable it was not mandatory for the success of the study as the goal of consuming the diet at home was for the subjects to learn the approximate calorie value of the diet by physiological feedback. The caliber of the subjects recruited through the Columbia University newspaper and follow-up interviews suggested a high degree of compliance.

All subjects were told during the interview that we would measure breathing in a canopy system (see below), collect urine and blood for measurements, weigh the containers of food they would eat from, and ask them questions. They were told that none of the nutrients were experimental.

During the study, subject has access to opaque containers containing the liquid diet in flavors of their choice (vanilla, chocolate, strawberry, eggnog, black walnut, pecan, cherry, orange, and lemon) from 0900 to 2400 with no food available. Water was available ad libitum. They were told they could eat as much or as little of the diet as they wanted. Subjects had to consume a reasonable amount of the liquid diet during the initial control period in order to complete they study. Subjects who consumed less than 1500 kcal or more than 4500 kcal during the control period were not included in the study.

The study was divided into three periods: a control infusion of Ringer's lactate (RL, Period 1), nutrient infusion consisting of glucose, amino acids and fat (PPN or BCPPN, Period 2), and a final period of RL (Period 3). The initial control period was extended to ten (10) days in two (2) of the subjects receiving PPN to ensure that any decrease observed with PPN was not due simply to hospitalization.

Subjects were infused with 3 L RL with vitamins and electrolytes given through a peripheral vein from 0900 to 2100. The vitamins are amber colored and were divided between the first two (2) bottles as they were when PPN and BCPPN were infused so that every day throughout the study subjects received two (2) "yellow" bottles and a "clear" bottle. Simultaneously with the RL, a 500cc bottle of normal saline containing 40 kcal lipid emulsion (Intralipid TM) was infused (30 cc/hr). This solution closely resembled the Intralipid TM solution administered during Period 2. As a further precaution all IV contents throughout the study were placed in unlabelled, sterile evacuated containers. From 2100 to 0900 of every study day RL, in its normal container, was infused to keep the vein open (25 cc/hr).

Following this baseline period, subjects were infused according to the same schedule with 3 L of a glucose and amino acid solution (Aminosyn TM 10% (Abbott Laboratories, North Chicago, Ill.)) PPN; or a 50:50 mixture by nitrogen content of the Aminosyn TM 10% and BCAA TM 4% (Travenol Laboratories, Deerfield, Ill., BCPPN) and a separate infusion of fat (Intralipid TM (KabiVitrum, Anaheim, Cal.)) representing, respectively, 40%, 20%, and 40% of calories. The total caloric content of the infusion was adjusted for each subject to provide the equivalent of 85% of estimated resting energy expenditure (REE) (Table I).

TABLE I

Body Weight, Resting Energy Expenditure and Oral Intake During Period 1

| Subject | Body Weight (kg) | Resting Energy Expenditure (kcal) | Oral Intake (kcal) |
|---|---|---|---|
| PPN | | | |
| 1 | 98 | 2123 | 2341 ± 175 |
| 2 | 74 | 1701 | 2323 ± 101 |
| 3 | 76 | 2020 | 4115 ± 135 |
| 4 | 78 | 1881 | 2296 ± 48 |
|   | 82 ± 6 | 1931 ± 91 | 2769 ± 449 |
| BCPPN | | | |
| 5 | 78 | NA | 3533 ± 160 |
| 6 | 79 | 2346 | 3201 ± 192 |
| 7 | 101 | 2397 | 2240 ± 261 |
| 8 | 75 | NA | 2855 ± 121 |
|   | 83 ± 6 |   | 2957 ± 276 |

Mean ± SEM; NA, not available

Subjects therefore received glucose, amino acids and fat in an amount equal to 34%, 17%, AND 34% REE, respectively. The vitamins, electrolytes and trace elements administered during these periods exceeded minimum requirements. The exact composition is given in Table II.

TABLE II

Composition of IV Solutions and Liquid Diet (Ensure TM)

| Ringer's Lactate (per L) | | PPN and BCPPN (per L) | |
|---|---|---|---|
| Na | 130 mEq | NaCl | 50 mEq |
| Cl | 109 mEq | Ca | 4.7 mEq |
| K | 4 mEq | K PO4 | 6.6 mmoles |
| Ca | 3 mEq | MgSO4 | 8 mEq |
| Lactate | 28 mEq | | |
| Added | | Added | |
| KCl | 10 mEq | KCl | 10 mEq |
| multivitamins (first two bottles only) | | multivitamins (first two bottles only) | |
| trace elements: (ZnCl, CuCl, CrCl, MnCl) | | trace elements: (ZnCl, CuCl, CrCl, MnCl) | |

| Ensure TM (per 8 ounces) | | | | BCAA Solution* | |
|---|---|---|---|---|---|
| Corn Starch | | | | L-Amino-Acids | mM/DL |
| Sucrose | | | | Leucine | 9.56 |
| Sodium and Calcium Caseinates | | | | Isoleucine | 9.08 |
| Corn Oil | | | | Valine | 9.51 |
| Natural and Artificial Flavor | | | | Phenylalanine | 0.76 |
| Minerals | | | | Methionine | 0.77 |
| Multivitamins | | | | Lysine | 1.41 |
| Na | .20 g | Mg | 50 mg | Histidine | 0.55 |
| K | .37 g | Iodine | 19 μg | Threonine | 1.25 |
| Cl | .34 g | Mn | .50 mg | Tryptophan | 0.22 |
| Ca | .13 g | Cu | .24 mg | Alanine | 4.10 |
| P | .13 g | Zinc | 3.75 mg | Glycine | 4.87 |
| Multivitamins | | Iron | 2.25 mg | Arginine | 1.61 |
| | | | | Proline | 2.31 |
| | | | | Tyrosine | 0.07 |
| | | | | Serine | 1.14 |

*The branched-chain amino acids comprise about 60% of the amino acid infusion solution.

The PPN infusion was continued for six (6) days, the BCPPN for five (5) days, at which time subjects were again given RL, as described above, for the remainder of the experiment.

Food intake and body weight (with the subjects' back to the display on the scale so they could not see whether their weight changed) were measured daily. The first and last day's food intake data were not included in the data analysis. Data are presented as mean±SE. Subjects also completed questionnaires twice daily in which they rated subjective feelings of hunger and nausea on 10 cm visual analogue scales and described any cravings for food.

Oxygen consumption and carbon dioxide production were measured with the subject lying at rest using a rigid lucite head canopy developed in the Surgical Metabolic Unit laboratory (5). This permits frequent measurements of relatively long duration (three or four periods of 30-40 minutes each) evenly spaced throughout the day with minimal discomfort to the subject. Resting energy expenditure (REE) was calculated using traditional equations of indirect calorimetry. Elwyn et al., *Changes in Nitrogen Balance of Depleted Patients with Increasing Infusion of Glucose*, 32 Am. J. Clin. Nut., 1597 (1979).

Eight (8) subjects (21–30 years of age) within 10% of ideal body weight were studied (Table 1). Resting energy expenditure (Table 1) was measured throughout the study and values obtained during the initial control period were used to calculate the caloric value of the nutrient infusion. Data were unavailable for two (2) subjects in the BCPPN group and the Harris-Benedict equation was used. Harris et al., *Biometeric Studies of Basic Metabolism in Man*, Carnegie Inst. Pub., No. 279 (1979).

During the time these groups of subjects were studied, four (4) subjects consumed less then 1500 kcal/day of the liquid diet during the initial control period. Two (2) subjects consumed more than 5000 kcal/day during the initial control period and were also disqualified. A final subject from the PPN group was disqualified because he exhibited marked tendencies towards polydipsia. Average water intakes for all other subjects ranged from 0 to 500 cc/day during the initial control period and attended to remain constant for each subject during the study periods.

Caloric intakes were stable within each subject during the initial control period (Table I). There was significant decrease in oral intake when subjects were infused with PPN (FIG. 1; Table III).

Figure 2:
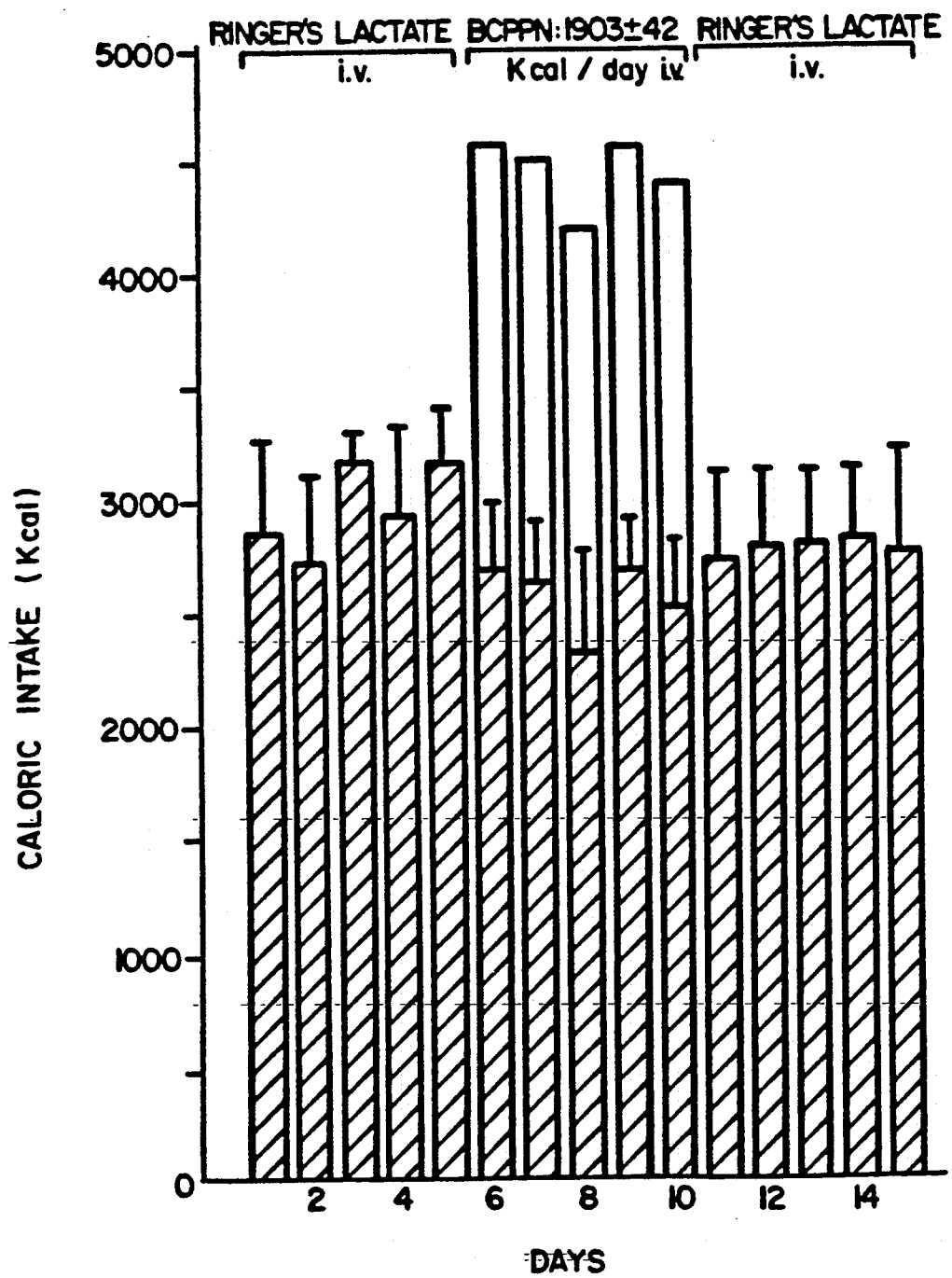
FIG. 2 shows oral (Dark) and intravenous (speckled) caloric intake in four subjects receiving Ringer's Lactate (Period 1), BCPPN (Period 2) and Ringer's Lactate (Period 3). Mean±SEM.

The decrease occurred in all subjects within a day or two of the beginning of the infusion. Oral intake had decreased to a plateau by the last two days of the infusion. In contrast, oral intake has decreased slightly but not significantly when the branched-chain amino acid enriched solution was used (FIG. 2; Table III).

TABLE III

| | Oral Intake (kcal) | | | |
|---|---|---|---|---|
| | Period 1 | Period 2 All Days | Period 2 Last 2 Days | Period 3 |
| PPN | 2769 ± 449 | 1548*** ± 447 | 1214** ± 365 | 1453† * ± 387 |
| BCPPN | 2957 ± 276 | 2549 ± 294 | 2584 ± 264 | 2779 ± 343 |

*Differs form oral intake during Period 1, p < 0.05
**Differs from oral intake during Period 1, p < 0.01
***Differs from oral intake during Period 1, p < 0.001
† Differs from oral intake during last two days of Period 2, p < 0.05

Intakes decreased slightly in three (3) of the four (4) subjects and did not change in the fourth subject.

Subjects receiving PPN decreased their intake by an amount that closely compensated for the amount of calories infused. The decrease in oral intake for the six (6) days of Period 2 was equal to 80±11% of the infused calories. By the last two days of the infusion period, oral intakes in the group receiving PPN had further decreased to an amount that compensated for 103±19% of the calories infused (individual values for the decrease in oral intake for subjects #1–4 were 81, 144, 124, and 62% of the calories infused, respectively). In subjects receiving the BCPPN infusion, oral intakes decreased by an amount that compensated for 21±9% of the infused calories over the five (5) day infusion period and did not change much over the five (5) days so that the decrease in intake compensated for 19±8% by the last two (2) days of the infusion (individual values for the decrease in oral intake for subjects #5–8 were 32, 27, 22, and −4% of the calories infused, respectively).

Relative to the last two days of the nutrient period, oral intakes increased during the third period (RL) in subjects receiving PPN even though oral intakes remained significantly decreased relative to the initial control period (Table III). Oral intakes increased in intake during the infusion period; oral intakes were therefore slightly but not significantly increased during the third period relative to the infusion period.

Body weights fluctuated slightly during the first two (2) periods in subjects receiving PPN and decreased approximately 1.5 kg during the final period when intakes were low. Body weights increased gradually in three (3) of the four (4) subjects receiving BCPPN by approximately 2.5 kg over the course of the study (BW did not change over the course of the study in subject #7).

Assessment was made of how hungry subjects were at 9 a.m. and 4 p.m. daily. There were no differences during the three (3) infusion periods or between the groups (average values ranged from 1.1 to 2.7 cm on a 10 cm visual analogue scale).

Three (3) of the four (4) subjects in the PPN group consistently reported food cravings (#1, 2, 4) throughtout the study; two (2) of the (4) subjects in the BCPPN group occasionally reported food craving (#5, 6) and the other two (2) never did.

Although, we are not certain of the physiological mechanism which causes the observed influence on appetite, it has been observed that the administration of the branched-chain amino acids, valine, leucine, and isoleucine to may result in decreased brain uptake of tryptophan, an amino acid which serves as the precursor for serotonin synthesis. This in turn may lead to decreased synthesis of brain serotonin, a central respiratory depressant. Takala et al., *Changes in Respiratory Control Induced by Amino Acid Infusions*, Crit. Care (May, 1988); Kinney, *Use of Branched-Chain Amino Acid Infusion to Influence Ventilation*, U.S. Ser. No. 904,715. Serotonin has been implicated as a neurotransmitter in the control of food intake. Blundell, *Is There a Role for Serotonin (5-hydroytryptamine) in Feeding?*, J. Obes. 15 (1977).

EXAMPLE 2

Studies were performed on six healthy male subjects. Subjects were maintained on a standard liquid diet composed of 40% carbohydrates (CHO), 40% fat, and 20% protein for 21 days. During this period, subjects were admitted at 5 p.m. three times at one week intervals. The morning after admission subjects received one of the following regimens: Ringer's Lactate (RL), Parenteral Nutrition (PN) as glucose, fat and amino acids (PN), or PN with half of the amino acids replaced with BCAA (BCPN). The infusions were begun at 9 a.m.; at 3 p.m. Gastric Emptying (GE) was measured by scintigraphic technique using a Gamma-camera, after subjects had consumed 500 cc (500 kcal) of a liquid test meal tagged with 200 micro Cu of technetium 99m DTPA. Radioactive counts were obtained every two minutes for ninety minutes with the subjects in the sitting position.

Figure 3:
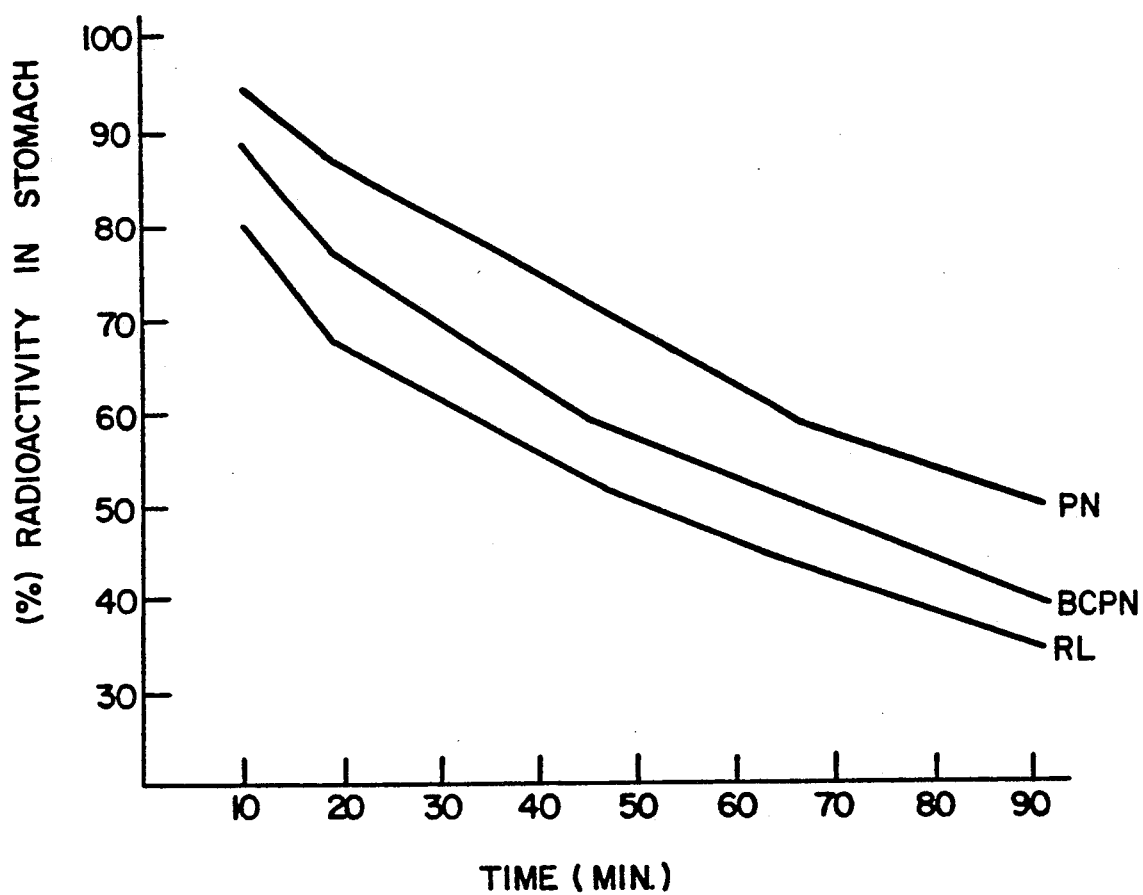
FIG. 3 shows percent radioactivity in stomach vs. time.

Values for GE, expressed as the remaining radioactivity in the stomach at sixty minutes (Mean±SEM) were: R-L: 44.8±5.9; PN: 63.5±6.8; BCPN: 53.4±6.5. PN decreased GE as compared to the control period (PN vs. R-L: $p<0.05$) (FIG. 3). Futhermore, it has been observed that increasing from 25 to 85% the BCAA/AA ratio in PN (BCPN) results in a stimulation of GE relative to PN.

While in the foregoing, an embodiment of the invention has been disclosed, it will be understood by those skilled in the art that many of these details may be varied without departing from the spirit and scope of the invention.

What is claimed is:

1. A method to decrease the risk of aspiration of gastric contents as a result of the administration of anesthesia to a patient comprising:
   parenterally administering preoperatively a therapeutically effective amount of an amino acid solution including branched chain amino acid.

2. The method of claim 1 wherein said branched-chain amino acid comprises 85% of the amino acid solution.

3. A method to decrease the risk of aspiration of gastric contents as a result of the administration of anesthesia to a patient comprising parenterally administering preoperatively a therapeutically effective amount of an infusion solution wherein the amino acid solution comprises about:

| L-Amino-Acids | mM/DL |
|---|---|
| Leucine | 9.56 |
| Isoleucine | 9.08 |
| Valine | 9.51 |
| Phenylalanine | 0.76 |
| Methionine | 0.77 |
| Lysine | 1.41 |
| Histidine | 0.55 |
| Threonine | 1.25 |
| Tryptophan | 0.22 |
| Alanine | 4.10 |
| Glycine | 4.87 |
| Arginine | 1.61 |
| Proline | 2.31 |
| Tyrosine | 0.07 |
| Serine | 1.14 |

4. A method for decreasing the risk of aspiration of gastric contents as a result of the administration of anesthesia to a patient comprising the steps of:
preoperatively administering a therapeutically effective amount of an amino acid parenteral solution including leucine, isoleucine, and valine.

5. The method of claim 4 wherein leucine, isoleucine, and valine comprise approximately 85% of the amino acid parenteral solution.

6. The method of claim 4 wherein the ratio of leucine to isoleucine to valine is approximately 1:1:1.

7. The method of claim 4 wherein the amino acid solution comprises about:

| L-Amino-Acids | mM/DL |
|---|---|
| Leucine | 9.56 |
| Isoleucine | 9.08 |
| Valine | 9.51 |
| Phenylalanine | 0.76 |
| Methionine | 0.77 |
| Lysine | 1.41 |
| Histidine | 0.55 |
| Threonine | 1.25 |
| Tryptophan | 0.22 |
| Alanine | 4.10 |
| Glycine | 4.87 |
| Arginine | 1.61 |
| Proline | 2.31 |
| Tyrosine | 0.07 |
| Serine | 1.14 |

* * * * *